United States Patent
Erdman, III et al.

(10) Patent No.: US 9,239,277 B2
(45) Date of Patent: Jan. 19, 2016

(54) MATERIAL MECHANICAL CHARACTERIZATION METHOD FOR MULTIPLE STRAINS AND STRAIN RATES

(75) Inventors: Donald L. Erdman, III, Knoxville, TN (US); Vlastimil Kunc, Knoxville, TN (US); Srdjan Simunovic, Knoxville, TN (US); Yanli Wang, Knoxville, TN (US)

(73) Assignees: UT-BATTELLE, LLC, Oak Ridge, TN (US); OAK RIDGE ASSOCIATED UNIVERSITIES, Oak Ridge, TN (US)

( * ) Notice: Subject to any disclaimer, the term of this patent is extended or adjusted under 35 U.S.C. 154(b) by 677 days.

(21) Appl. No.: 13/469,525

(22) Filed: May 11, 2012

(65) Prior Publication Data

US 2012/0287248 A1 Nov. 15, 2012

Related U.S. Application Data

(60) Provisional application No. 61/485,163, filed on May 12, 2011.

(51) Int. Cl.
  *G01N 3/08* (2006.01)
  *G01N 3/06* (2006.01)

(52) U.S. Cl.
  CPC .............. *G01N 3/08* (2013.01); *G01N 3/068* (2013.01); *G01N 2203/0298* (2013.01); *G01N 2203/0647* (2013.01)

(58) Field of Classification Search
  CPC ....................................................... G01N 3/08
  See application file for complete search history.

(56) References Cited

U.S. PATENT DOCUMENTS

| 4,020,723 | A | 5/1977 | Nix |
| 5,237,876 | A | 8/1993 | Liu |
| 2005/0279172 | A1 | 12/2005 | Schreier et al. |
| 2007/0209447 | A1* | 9/2007 | Christ et al. .................... 73/800 |
| 2009/0247871 | A1 | 10/2009 | Varghese et al. |

(Continued)

FOREIGN PATENT DOCUMENTS

| CN | 101655352 A | 2/2010 |
| JP | 6-160046 A | 6/1994 |

(Continued)

OTHER PUBLICATIONS

Ettemeyer, Material and Component Validation by Speckle Interferometry and Correlation Methods, Dec. 25, 2004.*

(Continued)

*Primary Examiner* — Sath V Perungavoor
*Assistant Examiner* — James Pontius
(74) *Attorney, Agent, or Firm* — Brinks Gilson & Lione

(57) ABSTRACT

A specimen for measuring a material under multiple strains and strain rates. The specimen including a body having first and second ends and a gage region disposed between the first and second ends, wherein the body has a central, longitudinal axis passing through the first and second ends. The gage region includes a first gage section and a second gage section, wherein the first gage section defines a first cross-sectional area that is defined by a first plane that extends through the first gage section and is perpendicular to the central, longitudinal axis. The second gage section defines a second cross-sectional area that is defined by a second plane that extends through the second gage section and is perpendicular to the central, longitudinal axis and wherein the first cross-sectional area is different in size than the second cross-sectional area.

33 Claims, 12 Drawing Sheets

(56) References Cited

U.S. PATENT DOCUMENTS

2010/0016711 A1  1/2010  Kheradvar et al.
2011/0005332 A1* 1/2011  Wang et al. .................... 73/856

FOREIGN PATENT DOCUMENTS

| JP | 2003-247922 A | 9/2003 |
| JP | 2008-96377 A | 4/2008 |
| WO | WO 2010/090294 A1 | 8/2010 |
| WO | WO 2011/045351 A1 | 4/2011 |

OTHER PUBLICATIONS

Principle of Digital Image Correlation,correlatedcolutions,Aug. 27, 2003.*

Srdjan Simunovic, High Strain-Rate Characterization of Magnesium Alloys, May 9, 2011.*

Author unknown, Abstract of "Full-field dynamic displacement and strain measurement using 3D image correlation photogrammetry: Part I" by Schmidt, T., et al. at Experimental Techniques, vol. 27, Issue 3, May 2003, pp. 47-50, Abstract available at http://www.scopus.com/record/display.url?eid=2-s2.0-0038104687 . . . as of May 4, 2011, one page.

Author unknown, p. 47 of "Full-field dynamic displacement and strain measurement using 3D image correlation photogrammetry: Part I" by Schmidt, T., et al. at Experimental Techniques, vol. 27, Issue 3, May 2003, pp. 47-50, reference available at http://onlinelibrary.wiley.com/doi/10.1111/j.1747-1567.2003.tb0011 . . . as of May 4, 2011, two pages.

Author unknown, Abstract of "A three-dimensional digital image correlation technique for strain measurements in microstructures" by Verhulp, E., et al. at Journal of Biomechanics, vol. 37, Issue 9, Sep. 2004, pp. 1313-1320, Abstract available at http://www.jbiomech.com/article/S0021-9290(04)00004-1/abstract as of May 4, 2011, two pages.

Author unknown, Abstract of "Full field strain measurement during a tensile split Hopkinson bar experiment" by Gilat, A., et al. at J. Phys. IV France, vol. 134, 2006, pp. 687-692, Abstract available at http://jp4.journaldephysique.org/index.php?option=com_article&acc . . . as of May 4, 2011, one page.

Wang, Y. et al., "Characterization of High-Strain Rate Mechanical Behavior of AZ31 Magnesium Alloy Using 3D Digital Image Correlation," Advanced Engineering Materials, vol. 13, No. 10, published online May 17, 2011, pp. 943-948.

Tiwari, V., et al., "Application of Digital Image Correlation in Impact Testing," source unknown, date of article unknown, 2 pages.

* cited by examiner

HSLA

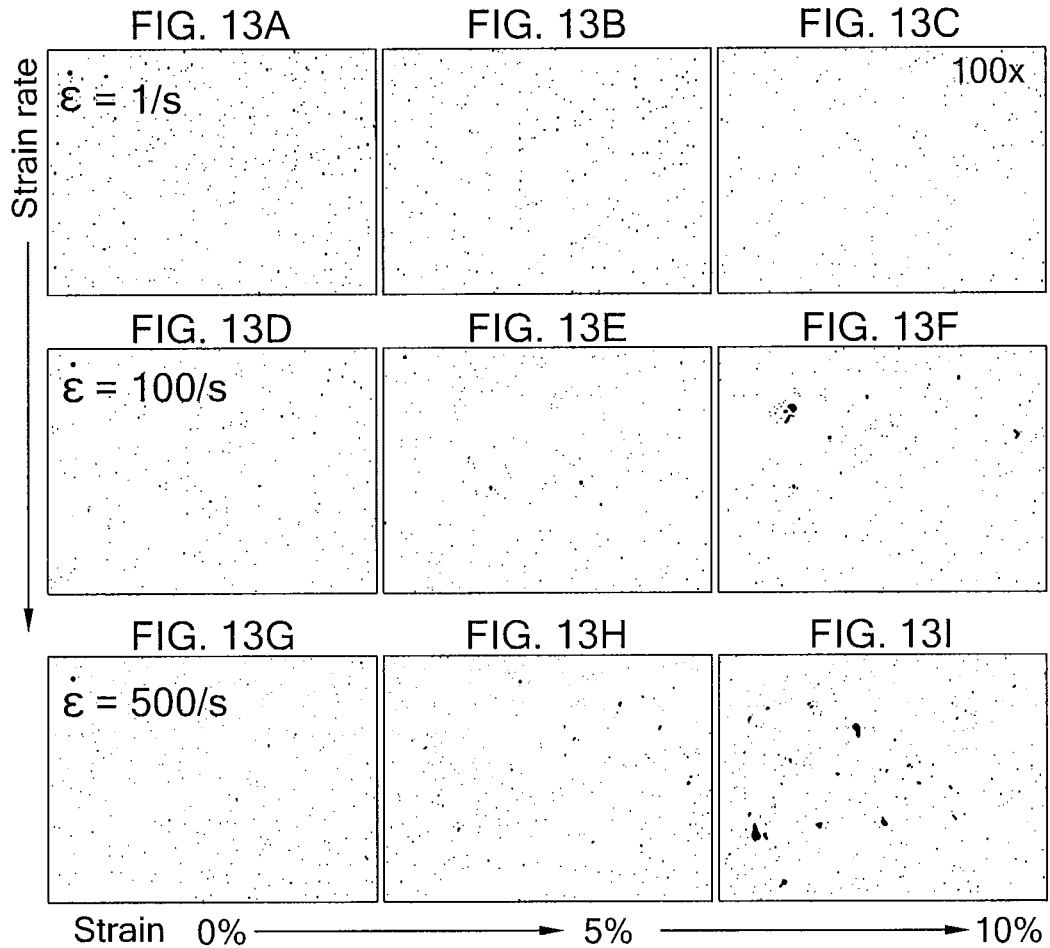
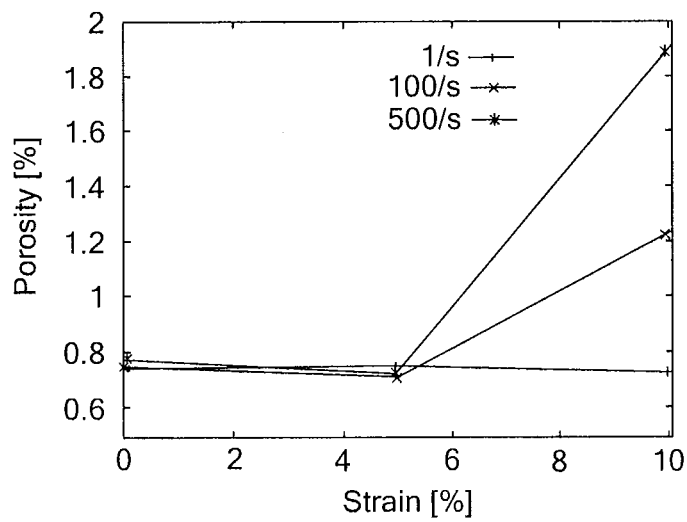
FIG. 14

MATERIAL MECHANICAL CHARACTERIZATION METHOD FOR MULTIPLE STRAINS AND STRAIN RATES

Applicants claim, under 35 U.S.C. §119(e), the benefit of priority of the filing date of May 12, 2011 of U.S. Provisional Patent Application Ser. No. 61/485,163, filed on the aforementioned date, the entire contents of which are incorporated herein by reference.

This invention was made with government support under Contract No. DE-AC05-00OR22725 awarded by the U.S. Department of Energy. The government has certain rights in the invention.

BACKGROUND

1. Field of the Invention

The present invention pertains to systems and methods for characterizing mechanical properties when subject to multiple strains and strain rates.

2. Discussion of Related Art

With the rising cost of fuel, automobile manufacturers are looking for ways to improve fuel mileage. One way to do this is to use lightweight materials, such as alloys of Magnesium (Mg), when manufacturing an automobile. In the case of using Magnesium alloys, automobile manufacturers desire to use them because of their high strength-to-weight ratios. The application of magnesium alloys in the automobile industries will satisfy the goal of vehicle weight reduction and fuel efficiency improvement.

Before a material is used in an automobile, a number of information is needed. For example, mechanical properties under impact, damage and failure characterization, material and failure models and Finite Element Models (FEM) technology need to be determined. In addition, methods for material characterization under impact need to be developed. In the case of Magnesium alloys, little information regarding crashworthiness of the material is available. With that said, there are differences between the mechanical properties of conventional materials, such as High-Strength Low-Alloy Steel (HSLA), and Magnesium alloys. For example, as shown in FIGS. 1(a)-(f) the impact energy dissipation in HSLA during a crashworthiness test occurs by a different process than in a Magnesium alloy tube as shown in FIGS. 2(a)-(f). Faced with the difference in mechanical properties, current automobile designs that employ lightweight materials, such as Magnesium alloys, result in overdesigned components in order to compensate for the uncertainties in the deformation and failure mechanisms. Such overdesigning can be avoided by understanding the initiation and evolution of internal state and failure processes in the lightweight materials as functions of loading type and loading rates. Reducing uncertainties in component design would greatly improve the overall vehicle system reliability and enable weight reduction of the automobile.

Another property to test for a material is their response at different strain rates. Testing at low (quasi static) rates is performed in order to observe the situation when the system is in equilibrium at all times. At the other end of the spectrum, fast rate tests have been performed wherein a single impact pulse travels through the system. A more problematic area of interest is so-called intermediate rate tests performed in the range of between 1/s and 1000/s with multiple wave reflections in the system. This area is important because maximum strain rates are in the interval of 10-1000/s for automotive crashes. For intermediate rates, it is difficult to establish dynamic equilibrium in the sample and the system and it is a fact that intermediate strain rate tests have not been established.

With the above said regarding strain rates measurements, it is important to apply certain principles to the measurement of strain rates for lightweight materials. Such principles include: reducing mass in the system; developing lightweight load cells and sensors; understand and control oscillations in the system; and combine multiple measurement techniques for the same data.

One way to understand the structure of materials, such as lightweight materials, is to study the response and microstructure changes in the design of the materials. Material mechanical response and microstructure changes, such as microstructure defect evolution, are often dependent on the levels of imparted strains and strain rates. The changes in microstructure can provide understanding about processes of material mechanical degradation that can lead to structural failure. Many materials exhibit different mechanical response when loaded by different deformation rates. This property is called strain rate sensitivity and is conventionally examined by using multiple specimens and tensile tests.

For tensile test configurations, standard dog-bone specimens (ASTM E8) are used. For the sample geometry of standard dog-bone specimens, uniform deformation is achieved within the gage section and the measured strains and strain rates are related to the displacements in this region. In order to characterize the evolution of an internal state of a material at different rates of strain, it is required to instantly stop (interrupt) the deformation from a current loading speed. This interruption of the deformation is possible at very low loading speeds, but at velocities necessary to generate strain rates of 1/s and higher, the inertia of the loading equipment and control system makes this task impractical using conventional test methods. Performing strain-interrupted tests using dog-bone specimens becomes exceedingly difficult, if not impossible, at high rate testing speeds. Complicated testing fixtures have been proposed and have shown to be impractical at high rates of strain. These fixtures add extra mass in the loading train of the testing equipment and consequently introduce additional oscillations that reduce the quality of the measurements. Low (quasi-static) rate tests—entire system is in equilibrium at all times.

Note that conventional methods of calculating displacement or strains for materials in general from stroke (i.e., the actuator motion) are not accurate. For example, at low strain rate (1/s), strain calculated from stroke tends to overestimate the average strain of the gage section. At high strain rate (500/s), strain calculated from stroke tends to underestimate the average gage section strain. Such conventional methods give inaccurate measurements that need to be filtered and cannot provide data for small strains and for high strain rates. Furthermore, at high strain rates conventional methods results in the sample being difficult to control and an increase in measurement problems as the speed is increased.

Thus, there is a need for new testing methodologies and material information for the strain rates of interest in vehicle design when lightweight materials are employed. In particular, systems and methods need to be developed that can measure a wide range of strain rates from low to intermediate to high rates. It is envisioned that such systems and methods would employ multiple types of sensors, wherein one type of sensor would be configured to measure one range of rates and other types of sensors would be configured to measure other ranges of rates. In such a system, there would be a transition going from one type of sensor to another. Other parameters to be measured by new methods and systems would be: 1)

strain-interrupted tests at high rates, 2) methods for characterization of material property degradation (damage) evolution under high rates, 3) methods for failure characterization at high rates, 4) constitutive models for FEM simulations, and 5) investigating formation and growth of voids using microscopy for strains and strain rates of interest.

SUMMARY OF THE INVENTION

One aspect of the present invention regards a specimen for measuring behavior of a material under multiple strain rates with only a single strain test. The specimen including a body having a first end, a second end and a gage region disposed between the first end and the second end, wherein the body has a central, longitudinal axis passing through the first end and the second end. The gage region includes a first gage section and a second gage section, wherein the first gage section defines a first cross-sectional area that is defined by a first plane that extends through the first gage section and is perpendicular to the central, longitudinal axis. The second gage section defines a second cross-sectional area that is defined by a second plane that extends through the second gage section and is perpendicular to the central, longitudinal axis and wherein the first cross-sectional area is different in size than the second cross-sectional area.

A second aspect of the present invention regards a system for characterizing material behavior under multiple strain rates using a single specimen in one test, the system including a device for applying a load, the device comprising a first jaw and a second jaw, the device capable of applying strain loads at greater than 500 inches per second. A specimen having a body with a first end, a second end and a gage region disposed between the first end and the second end, wherein the first end is engaged by the first jaw and the second end is engaged by the second jaw, wherein the body has a central, longitudinal axis passing through the first end and the second end, wherein the gage region comprises a first gage section and a second gage section, wherein the first gage section defines a first cross-sectional area that is defined by a first plane that extends through the first gage section and is perpendicular to the central, longitudinal axis and the second gage section defines a second cross-sectional area that is defined by a second plane that extends through the second gage section and is perpendicular to the central, longitudinal axis and wherein the first cross-sectional area is different in size than the second cross-sectional area. The system further includes a camera focused at the specimen and generates an image of the specimen and a control and data acquisition unit that receives signals from the camera representative of the image and calculates a strain experienced by the specimen based on the signals.

A third aspect of the present invention regards a method for characterizing material behavior under multiple strain rates using a single specimen in one test. The method including applying a load to a specimen having a body with a first end, a second end and a gage region disposed between the first end and the second end, wherein the first end moves wherein the body has a central, longitudinal axis passing through the first end and the second end, wherein the gage region comprises a first gage section and a second gage section, wherein the first gage section defines a first cross-sectional area that is defined by a first plane that extends through the first gage section and is perpendicular to the central, longitudinal axis and the second gage section defines a second cross-sectional area that is defined by a second plane that extends through the second gage section and is perpendicular to the central, longitudinal axis and wherein the first cross-sectional area is different in size than the second cross-sectional area. The method further including generating an image of the specimen when a first deformation is experienced by the specimen and generating a second image of the specimen when a second deformation is experienced by the specimen. The method including calculating strains experienced by the specimen at the first and second deformations.

One or more aspects of the present invention provide the advantage of reducing the number of samples needed for material measurements.

One or more aspects of the present invention provide the advantage of measuring multiple strain rates in an efficient manner.

One or more aspects of the present invention provide the advantage of testing the structural characteristics of lightweight materials to be sued for automobiles in an efficient manner.

One or more aspects of the present invention provide the advantage of reducing the number of required tests for characterization of material strain rate sensitivity.

One or more aspects of the present invention provide a new capability of imparting prescribed strains at high strain rates and thereby enables characterization of material internal state evolution in this loading regime.

Further characteristics and advantages of the present invention will become apparent in the course of the following description of an exemplary embodiment by the drawings.

BRIEF DESCRIPTION OF THE DRAWINGS

FIGS. 13A-I show void profile examples;

FIG. 14 shows the measurement of porosity versus strain and strain rate at various strain rates;

DETAILED DESCRIPTION OF THE PREFERRED EMBODIMENTS

Figure 1:
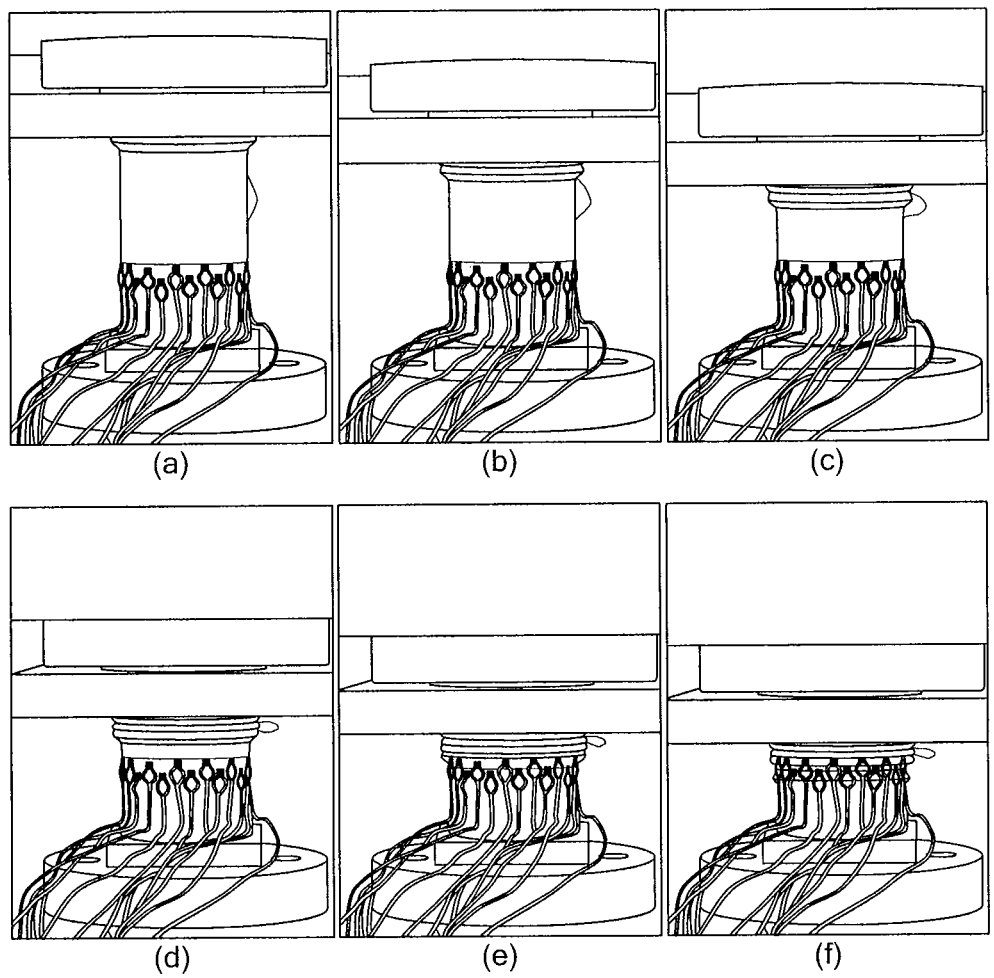
FIGS. 1(a)-(f) show impact energy dissipation in HSLA during a crashworthiness test.
Figure 2:
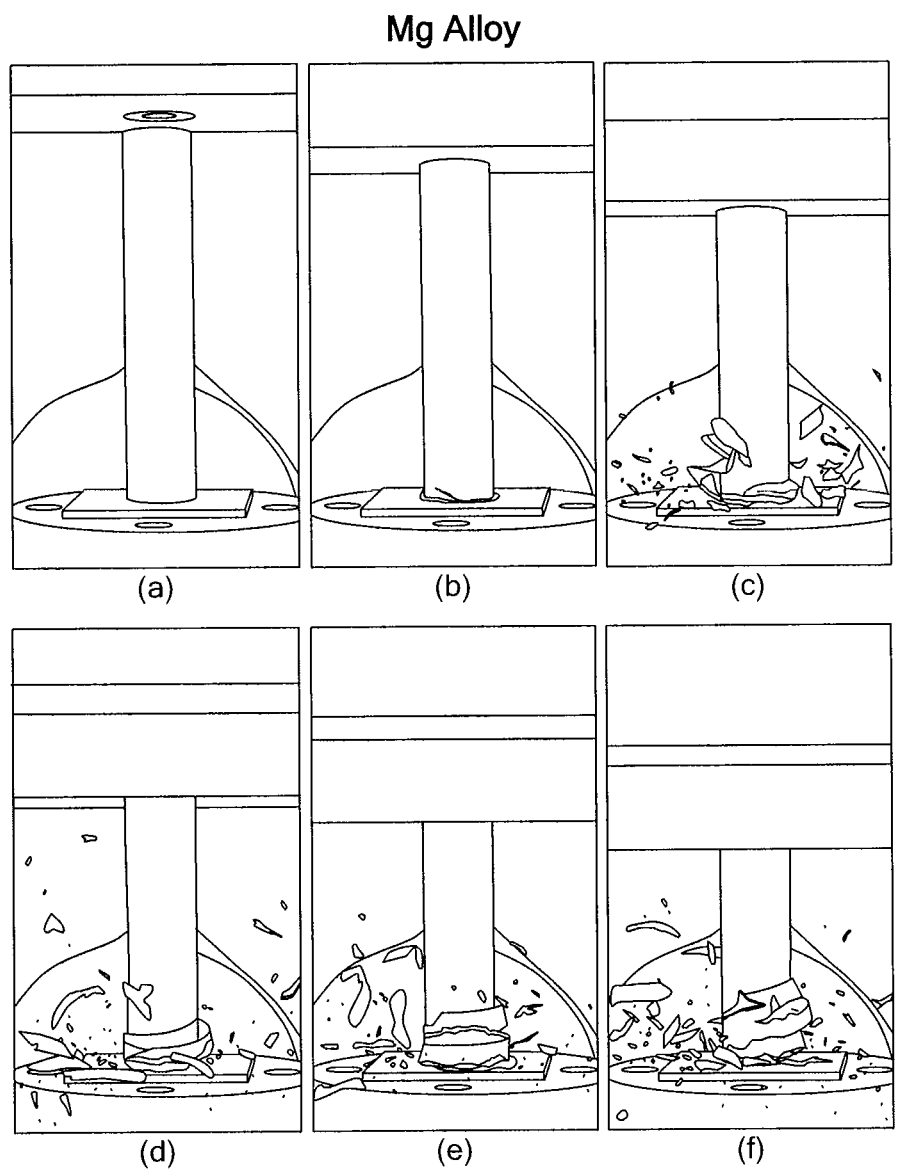
FIGS. 2(a)-(f) show impact energy dissipation in a Magnesium alloy during the same crashworthiness test as in FIGS. 1(a)-(f)
Figure 3:
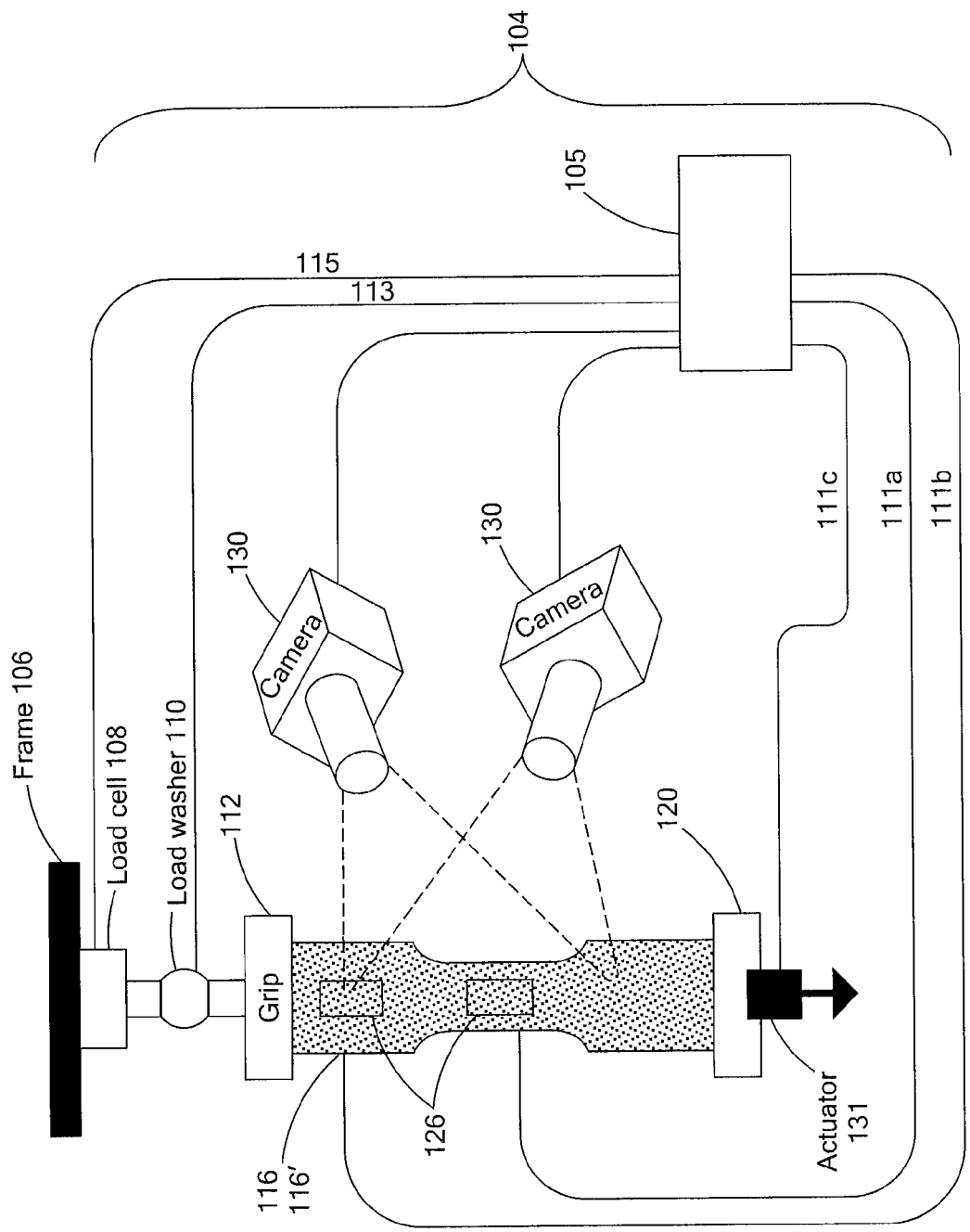
FIG. 3 schematically shows an embodiment of a measuring system in accordance with the present invention.
Figure 7:
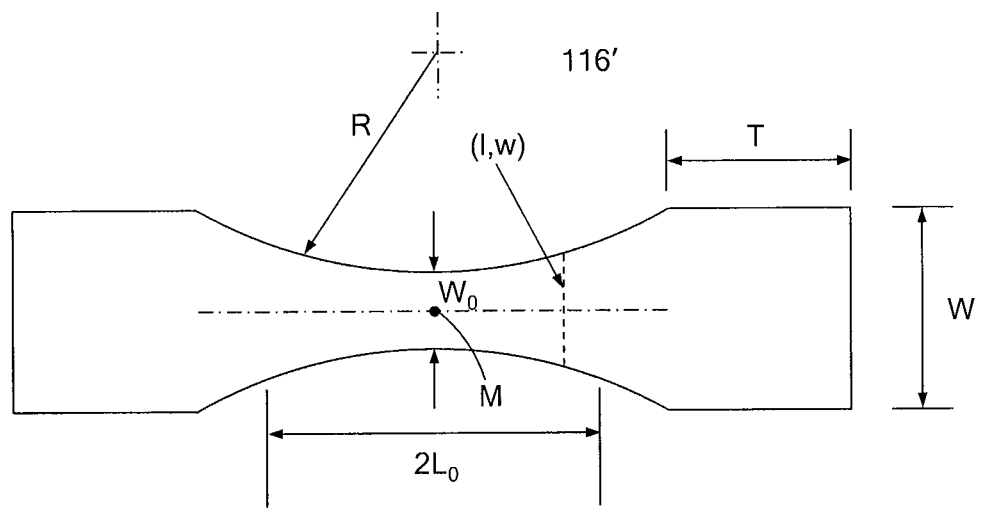
FIG. 7 shows a second embodiment of a specimen to be used with the measuring system of FIG. 3 in accordance with the present invention.

As schematically shown in FIG. 3, a measuring system 100 that performs various measurements regarding strain and strain rates is provided. The hydraulic test system includes a test frame 106 and a hydraulic actuator 131 that pulls down on a grip 120. Such pulling motion results in deformation of the specimen 116, 116' (specimen 116' of FIG. 7 is shown, for example). The operation mechanism of the hydraulic system is described by Y. Wang et al. entitled "Characterization of High Strain Rate Mechanical Behavior of Az31 Magnesium Alloy using 3D Digital Image Correlation." The deformation is measured via a 3D Digital imaging correlation system 104 that can generate a full field displacement map. The system 104 includes two high speed digital cameras 130 and a control and data acquisition unit 105. An example of a suitable digital camera 130 is the Photron FASTCAM SA5 which provides 7,500 frames per second (fps) at resolution of 1024×1024 pixels and reduced resolution operation to a maximum of 1,000,000 frames per second. The digital cameras 130 are staged so that the area of interest on the sample is visible to both cameras. Note that control and synchronization of multiple data sources is desired for accuracy at high speeds.

Prior to tensile testing, a standard calibration procedure is performed to determine the camera parameters, such as focal length, radial distortion coefficients, center position of the lens, skew of the sensor grid and the relationship between the two cameras 130. A rigid calibration grid with known spacing is used to perform the calibration. Within the depth of field, images are taken simultaneously while the calibration grid is placed to cover the image field and positioned to have tilt/rotation and translation along all three axes. An acceptable calibration for this study is when the standard deviation of residuals for a minimum 20 views of the calibration grid at various positions is less than 0.05 pixels.

During the deformation process, the cameras 130 receive images of an area of interest of the specimen. In the area of interest, a speckle pattern is present. The signals representative of the images of the speckle pattern present in the area of interest are then sent to control and data acquisition unit 105. The signals from each camera are synchronized and combined so that a three-dimensional full field deformation map is generated for a number of instances of the deformation process. Preferably, consecutive instances of time are separated from one another by an equal amount of time, with separations that can range from 10 s to $1\times10^{-6}$ s being possible. The three-dimensional full field deformation maps are formed in a well-known manner using software available under the trade name of VIC-3D 2010 Digital Image Correlation made by Correlated Solutions, Inc.

With the above described deformation maps, the control and data acquisition unit 105 using the above described VIC-3D 2010 Digital Image Correlation software is able to determine for each speckle in the area of interest how its position changes from one map to the next. In particular, the deformation strains are resolved by post-processing the sequential speckle images of the tested specimen 116 based on a pattern-matching algorithm, such as available from the commercial software VIC-3D 2010 (Correlated Solutions, Inc.). The standard deviation for strain measurements is about 60 microstrain. An example of the above mentioned measurement of strain using high speed cameras is described in the article by Y. Wang et al. entitled "Characterization of High Strain Rate Mechanical Behavior of Az31 Magnesium Alloy using 3D Digital Image Correlation," Advanced Engineering Materials, Vol. 13, No. 10, 2011, pp. 943-948.

Figure 4:
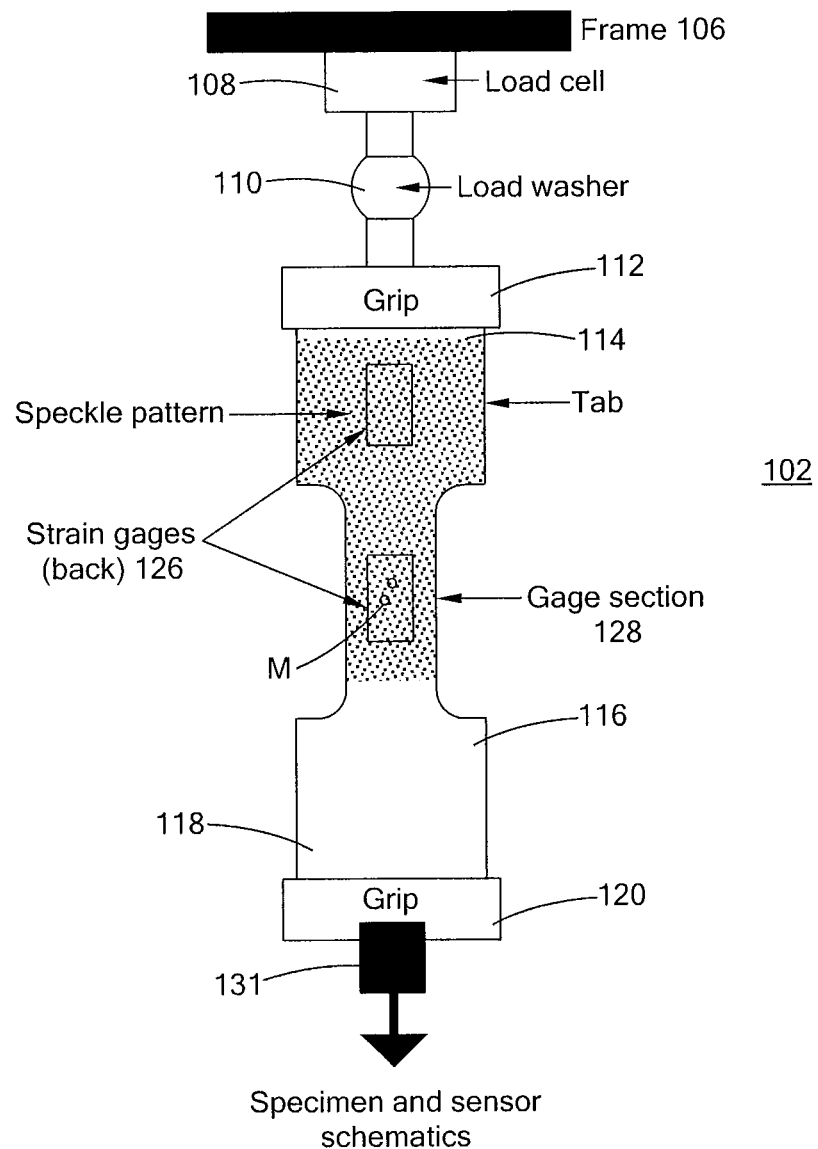
FIG. 4, schematically shows an embodiment of a hydraulic tensile machine to be used with the measuring system of FIG. 3 in accordance with the present invention.

As shown in more detail in FIG. 4, the pulling actuator 131 can be thought of as being part of a tensile machine 102 that includes a frame 106 to which a load cell 108 is attached. The load cell 108 and load washer 110 is in communication with control and data acquisition unit 105. Top grip 112 engages a top portion or tab 114 of the lightweight material sample 116. A bottom portion or tab 118 of the sample 116 engages a bottom grip 120. In FIG. 5A, fixture 124 engages the top 114 of the specimen 116 and allows the bottom 118 of the specimen 116 to pass through to engage the bottom grip 120. The mechanical stopper 125 is engaged to the bottom 118 of the specimen 116.

Figure 5B:
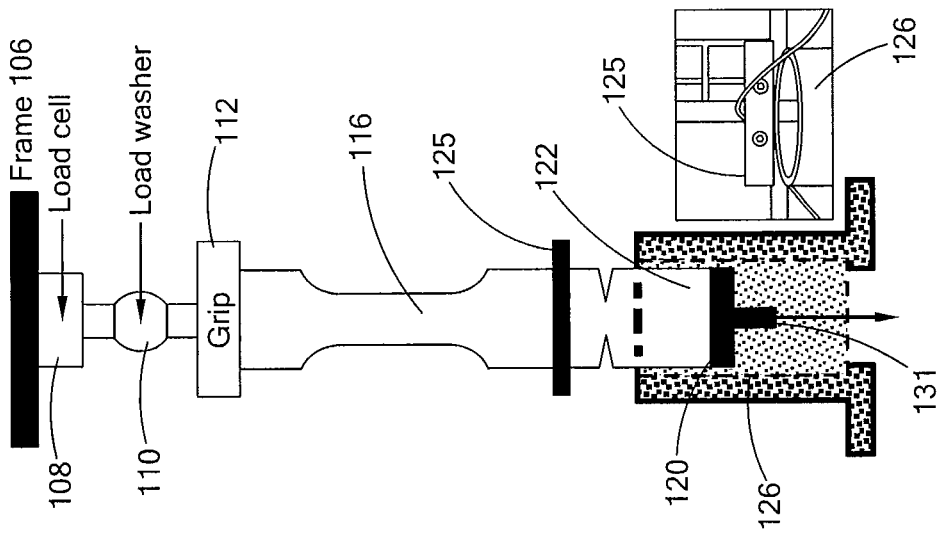
FIG. 5B shows a second embodiment of a test fixture to be used with the hydraulic tensile machine of FIG. 4 in accordance with the present invention.
Figure 5A:
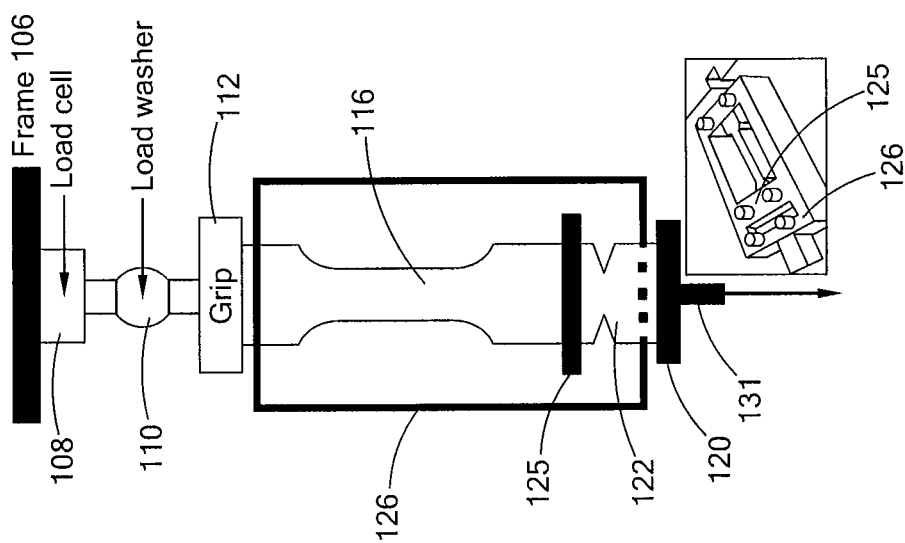
FIG. 5A shows a first embodiment of a test fixture to be used with the hydraulic tensile machine of FIG. 4 in accordance with the present invention.

An alternative test fixture 124' is shown in FIG. 5B. The amount of specimen deformation is defined by the spacing between the mechanical stopper 125 and the stationary part of the fixture 126 while the specimen is tested under tension. The specimen will break at the notch section after the mechanical stopper engages the stationary part of the fixture 126. The stationary part of the fixture 126 in FIG. 5A is a solid metallic frame with a through slot at the bottom to allow the specimen to pass through. The stationary part of the fixture 126 in FIG. 5B is a solid metallic tube.

As shown in FIG. 4, the specimen 116 includes strain gages 126 located at the top portion 114, central portion or gage section 128, and bottom portion 118. Each strain gage 126 is an electrical bridge circuit that indirectly measure a load applied to the strain gage in a well-known manner. Signals 111$a$, $b$ from the strain gages 126, signals 113 from the load washer 110 and signals 115 from the load cell 108 are sent to control and data acquisition unit 105. These signals are synchronized with the images from cameras 130 during the tensile test. The control and data acquisition unit 105 sends command signals 111$c$ to the actuator 131 to control its motion. Note that the control and data acquisition unit 105 sends command signals 111$c$ to the actuator for testing of the specimen and collects the data present in signals 111$a$, $b$, 113 and 115. Such collection of data is synchronized with the acquisition of images by system 104. In one embodiment, synchronization can be achieved by generating a 50 millisecond pulse on an M-series PXI-6259 multifunction IO board. This pulse is then simultaneously detected by the data acquisition and waveform generation tasks on the same PXI-6259 IO board that were programmatically configured pre-test. Similarly, a second board, such as the M-series PXI-6250 board, is also triggered off the same pulse along with the two high speed cameras in the imaging system. All triggers are synchronized through the PXI chassis in which the M-series cards are installed. The chassis backplane runs a 10 MHz system clock yielding 100 ns trigger synchronization.

In operation, the machine 102 may have the following properties:

Max Velocity=700 in/s (18.5 m/sec) over approx. 4 in (100 mm) Range;

Load Capacity: 9000 lbs (40 kN) static, 5500 lbs (25 kN) dynamic;

Total Stroke: 15.5 in (400 mm);

Working Stroke: approx. 7.0 in (175 mm) with slack adapter in the load train;

Control: MTS 407 servo-hydraulic controllers, with external command signal (drive file); and Synchronization and DAQ systems.

With the above discussion of the measuring system 100 in mind, some general principles of measurement and operation should be kept in mind. For example, elimination of noise (the mechanical vibration present in the dynamic test) in the system 100 is the most challenging task along with having the load cell fight the effect of inertia of the devices in order to keep accuracy at high rates. In the system 100, the strain gages 126 on the specimen 116 are used for strain and stress measurements in the central portion 128. In addition, optical strain measurements from the high speed cameras 130 are used for strain and stress measurements across the specimen 116. Measurements from 1) different sensors 126 located in the tab and gage sections, 2) the load washer 110 and 3) the load cell 108 are compared with optical measurements performed by the cameras 130 for different strain rates in order to establish correlations and estimate errors.

Figure 6:
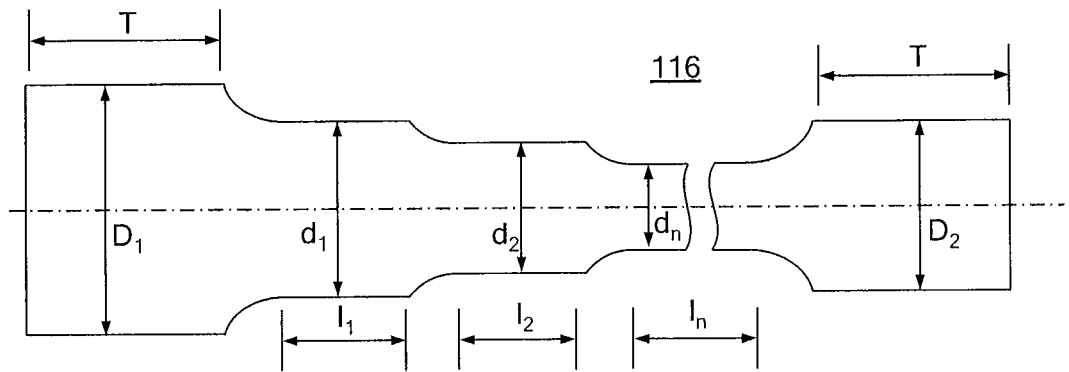
FIG. 6 shows a first embodiment of a specimen to be used with the measuring system of FIG. 3 in accordance with the present invention.

FIG. 6 shows an embodiment of a specimen 116 to be tested by the measuring system 100 of FIG. 3. Possible materials for the specimen 116 are AZ31 sheet metal, AM60B cast (top hat), AM60B unprocessed and Advanced High Strength Steels (AHSS). The goal of the specimen design is to enable application of a desired strain and strain rate distribution across the specimen gage length. The possibility of changing mechanical properties of a test specimen through mechanical work and/or thermal process in order to create desired property distribution and thereby tailor the strain and strain rate distribution is also envisioned. Specimen design enables application of desired strain under specific strain rate by ensuring specimen rupture at a prescribed location so that it is not necessary to insert additional fixtures (stoppers, displacement limiters) into the loading train.

In the specimen design of FIG. 6, a standard dog-bone specimen geometry is modified to have multiple gages sections (i.e., gage $I_1, I_2 \ldots I_n$) rather than a single gage. As shown in FIG. 6, the end portions having widths $D_1$ and $D_2$ are connected to the gages sections $I_1$ and—$I_n$, respectively via step portions that have a non-linear profile as viewed along a direction perpendicular to a central, longitudinal axis (see dashed lines) of the specimen. Similarly, the gage sections $I_1, I_2 \ldots I_n$ are connected to one another by step portions that have a non-linear profile as viewed along the direction perpendicular to the central, longitudinal axis. So, in contrast with the standard dog, bone specimen, the specimen of FIG. 6 has a multiple gage sections with changing cross-section areas, wherein the cross-sectional area of a particular gage section is constant along the length of the gage section and is defined by plane that extends through the gage section and is perpendicular to the central, longitudinal axis. Each gage length can be the same or different than each other. The total specimen length must be practically possible for the test instrument and the area of interest should fit into the digital imaging windows. Each gage has different width with $d_1 > d_2 > \ldots > d_n$ and the idea is to achieve yielding in $I_1$ after the minimum width gage reaches ultimate tensile strength. The initial specimen width dimensions can be estimated through the ratios between the yield strength and ultimate tensile strength, but the accurate strain and strain rate in each gage should be analyzed through 3D Digital Imaging Correlation via system 104.

FIG. 7 shows a specimen 116' that can achieve a continuous and infinite distribution of strains and strain rates. Possible materials for the specimen 116' are AZ31 sheet metal, AM60B cast (top hat), AM60B unprocessed and Advanced High Strength Steels (AHSS). Instead of a standard dog-bone gage section, this design has a gage with a curvature of R. The initial estimation of R is based on the ratio of the material ultimate tensile strength, $\sigma_{UTS}$, and yield strength, $\sigma_{ys}$, under static test rates. In other words, the specimen should yield at $+-L_0$ when the middle location fractures. For a sheet specimen with width $W_0$ and the desirable length for continuously varying the strains of $2L_0$, the curvature R, is given by equation (1) below. For accurate specimen design and analysis, Finite Element Modeling technique is suggested.

$$R = \sqrt{L_0^2 + \frac{W_0^2}{4}\left(\frac{\sigma_{UTS}}{\sigma_{ys}} - 1\right)^2} \quad (1)$$

The dimension of T and W are designed to fit in to the specimen grips. Other designs of this end tab (such as a pinhole design) can be employed. The only requirement is that the tab region is long and wide enough so that its deformation during the test does not affect the area of interest region of $2L_0$.

Note that other shapes for the specimen 116 are possible without departing from the spirit of the invention. The shape is determined by Finite Element Modeling.

The speed of the tensile test performed by system 100 should be chosen as the maximum speed of interest, and images of the sample should be taken during the test with appropriate frame rates to calculate the full-field displacement map within the area of interest using 3D digital image correlations.

Figure 8:
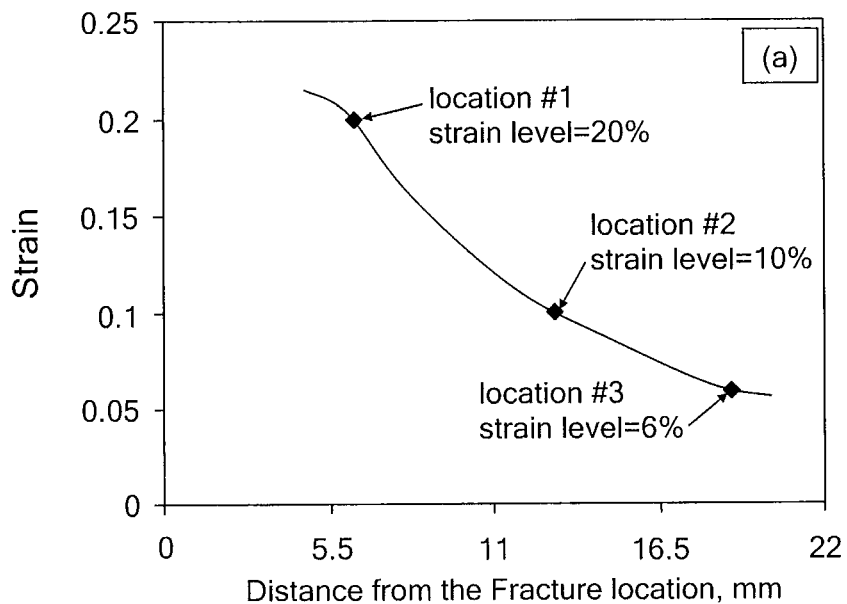
FIG. 8 shows a possible plot of strain versus distance from fracture location for the specimen of FIG. 7 using the measuring system of FIG. 3.
Figure 9:
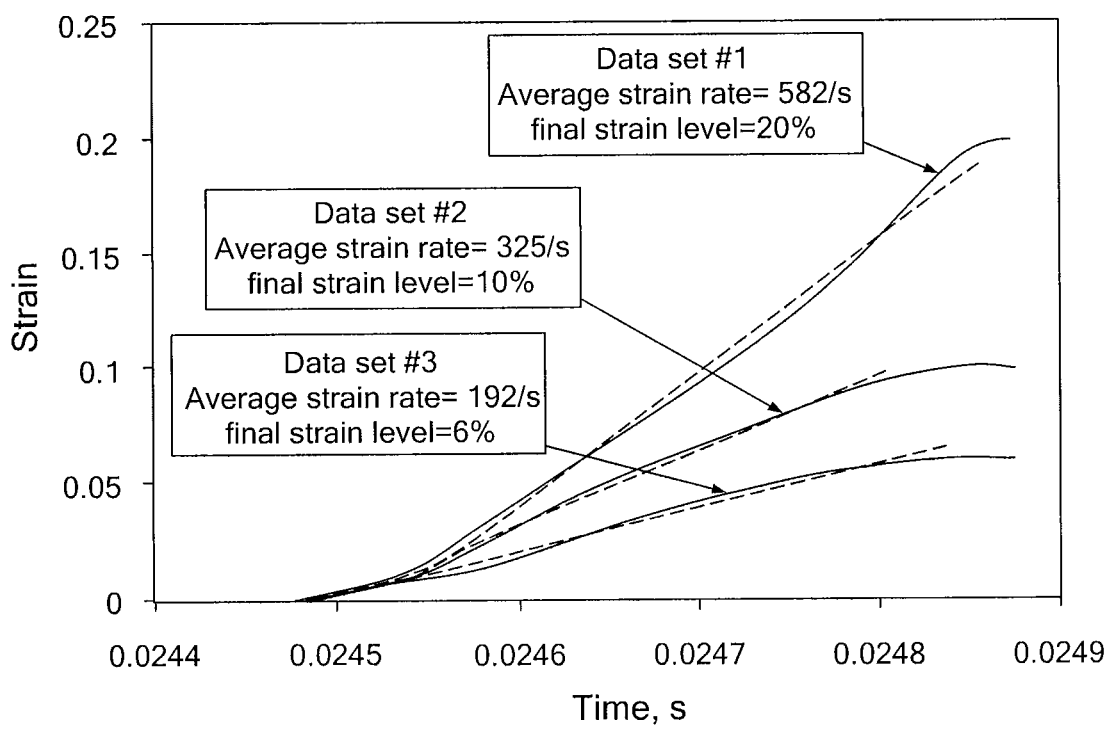
FIG. 9 shows a possible plot of strain versus time for the specimen of FIG. 7 using the measuring system of FIG. 3.

Using the specimen geometry shown in FIG. 7, the plastic strain will decrease continuously from the middle of the specimen to $+-L_0$, which can be shown from the full-field displacement map. Because of the difference in the strain levels, within the same amount of test duration time, continuous strain rates are also achieved at locations further away from the specimen center. Because the deformation of the specimen is recorded as a function of time, the strain and strain rate at each location (l, w) are resolved from the full field displacement map. FIGS. 8 and 9 show an example of one application of this specimen geometry to magnesium alloy AZ31. The specimen 116' has a curvature of 20 inches and is tested at a speed of 500 in/s. The strains and strain rates at each location of the interested area are resolved through the previously mentioned 3D digital image correlation. The specimen 116' experiences continuous deformation of 0–~23% within a one inch region that is centered about midpoint M of the specimen 116'. Results for three selected locations are shown in FIGS. 8-9 to demonstrate strain variation from 6% to 20% with strain rates from 192/s to 580/s. In particular, FIGS. 8-9 show the results at various distances (5.5 mm, 12 mm and 18 mm) from a fracture formed in the specimen 116'. The new method generates smoothly increasing strain path to the final strain and strain rate distribution.

In summary, with this test design, to achieve desired strains with various strain rates using a single specimen is emphasized. The present invention reduces the number of required tests for characterization of material strain rate sensitivity. Since there is no added mass, it results in a simpler and cheaper measurement process. It also provides a new capability of imparting prescribed strains at high strain rates and thereby enables characterization of material internal state evolution in this loading regime. Evidence of the advantages of the measuring system 100 of FIG. 3 and the samples of FIGS. 6 and 7 are discussed below.

Figure 10A:
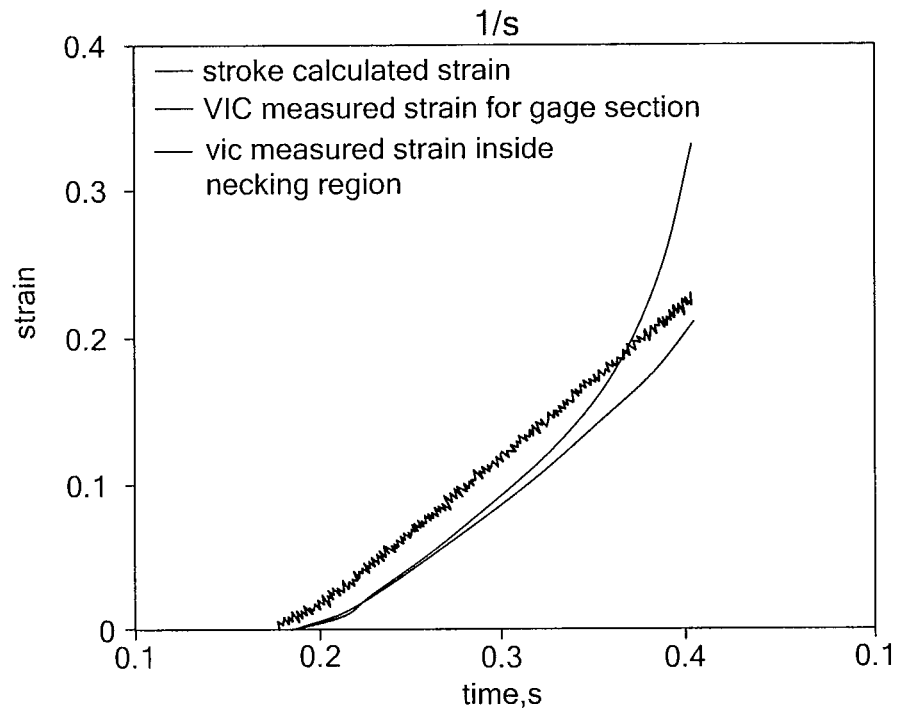
FIGS. 10A and 10B show the difference between the conventional method of calculating from stroke versus the use of digital image correlation (VIC) in the measuring system of FIG. 3.
Figure 10B:
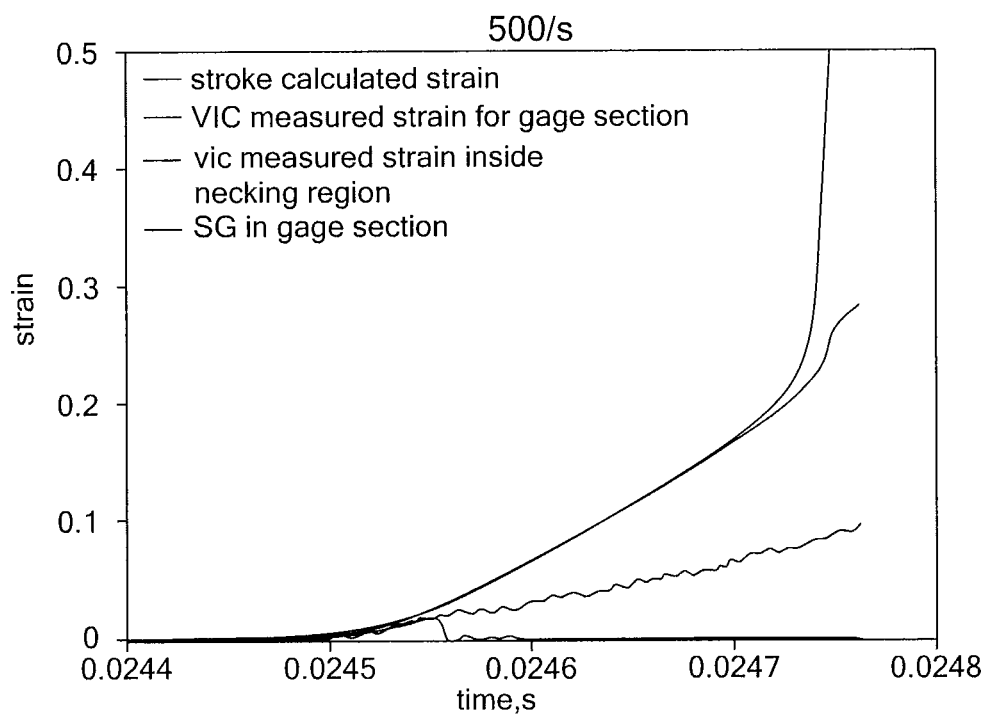

For example, FIGS. 10A and 10B show the difference between the conventional method of calculating from stroke versus the use of digital image correlation (VIC) in the measuring system 100. Indeed, digital image correlation enables measurement of strains well beyond the range of fast-response bondable foil gages.

Figure 11A:
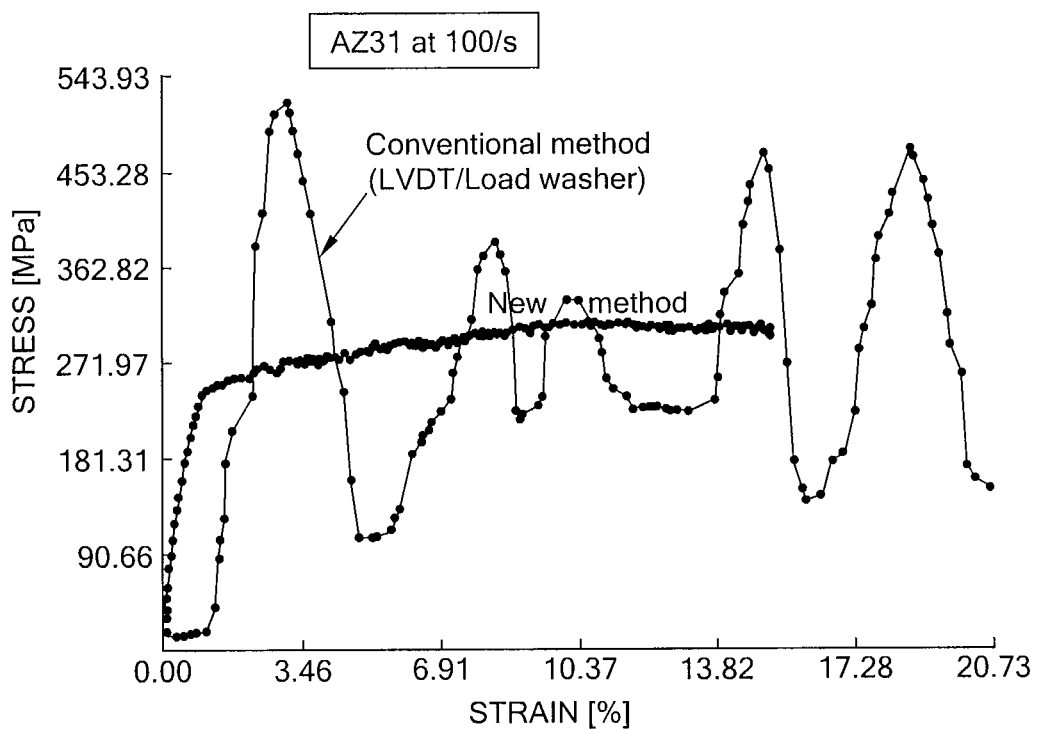
FIGS. 11A and 11B show the difference between the conventional method of testing strain rate using a LVDT/load washer versus the use of the samples of FIGS. 6 and 7 in the measuring system of FIG. 3.
Figure 11B:
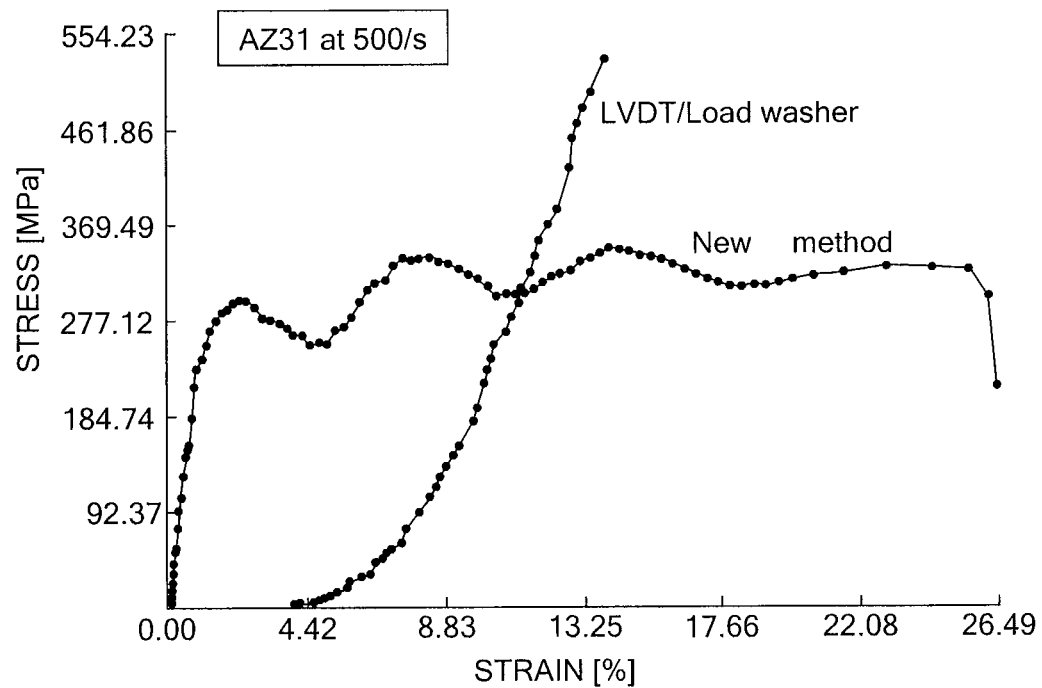
Figure 12A:
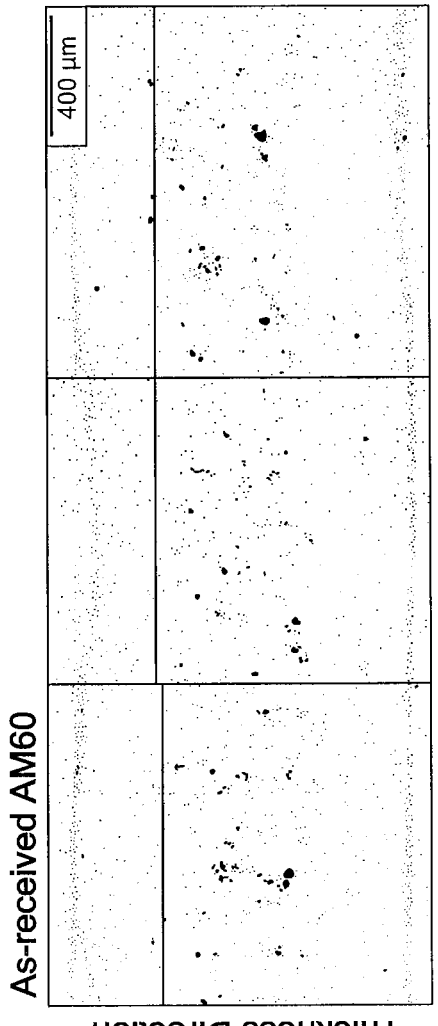
FIG. 12A, shows a non-uniform distribution of the pores/microstructure needs to be considered when locating an area of interest.
Figure 12D:
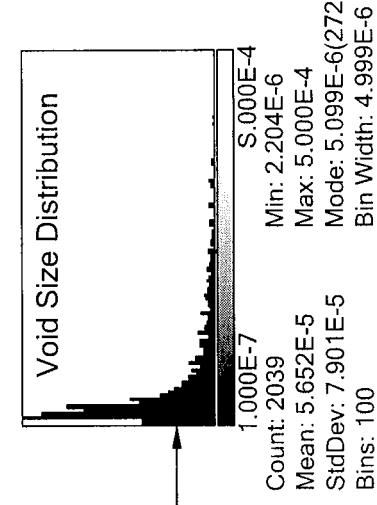
FIGS. 12B-D show how void statistics/data are generated by image processing.
Figure 12C:
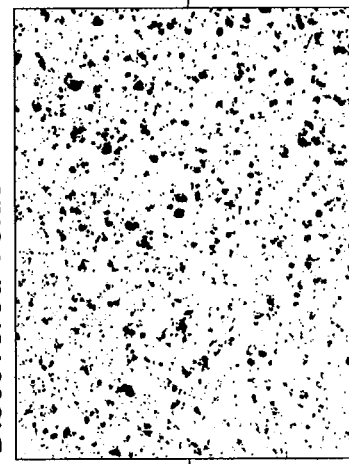
Figure 12B:
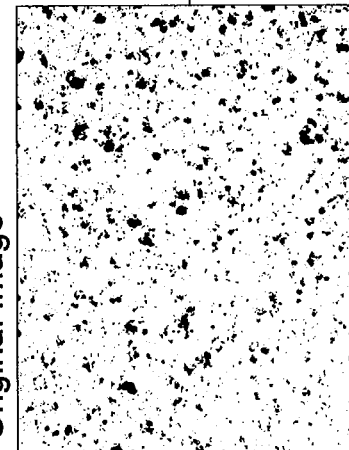

FIGS. 11A and 11B show the difference between the conventional method of testing strain rate using a LVDT/load washer versus the use of the samples of FIGS. 6 and 7 in the measuring system 100. Indeed, significant improvement in measurements of stresses, strains and strain rates in the intermediate strain rate regime is accomplished with the present invention.

Figure 16:
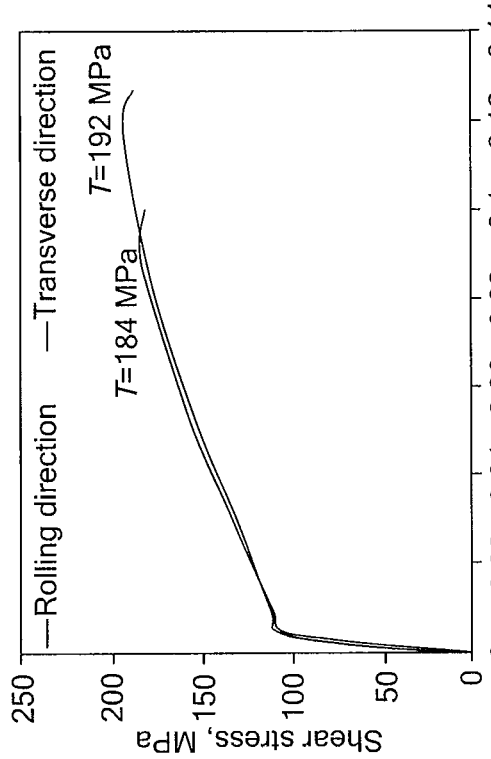
FIG. 16 shows the measurement by the system of FIG. 3 of the shear stress versus the shear strain.
Figure 15A:
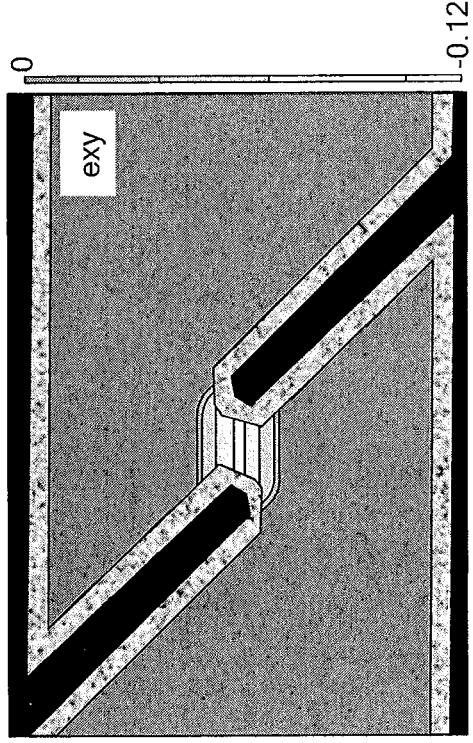
FIGS. 15A-B show an example of the evolution of the shear strains during a high-rate shear test run with the system of FIG. 3.
Figure 15B:
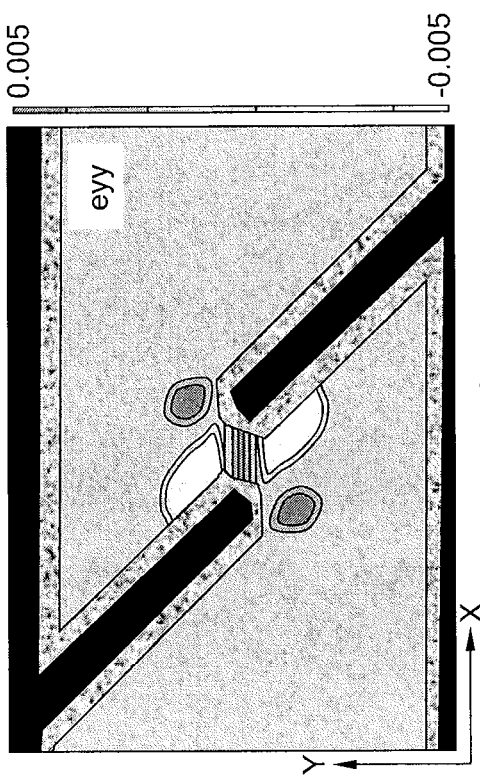

FIGS. 12-16 show various measurements performed by system 100 on the Magnesium alloy AM60. For example, FIG. 12A, shows a non-uniform distribution of the pores/microstructure needs to be considered when locating an area of interest. FIGS. 12B-D show how void statistics/data are generated by image processing. Such data can be used for calibration of micromechanics-based material and failure models for FEM simulations. FIGS. 13A-I show void profile examples and FIG. 14 shows the measurement of porosity versus strain. Measurements show that void nucleation and growth (damage) intensifies with strain rates for AM60. FIGS. 15A-B show shear normal stresses surrounding a slant notch and FIG. 16 shows the measurement by system 100 of the shear stress versus the shear strain. The system 100 generates reasonable strain distributions in the test specimen and test data correlates well with tension tests.

In summary, the new method specimen design and testing procedure can produce continuously varying levels of plastic strain achieved at various locations in the specimen and at different strain rates. The new specimen design also reduces the size of conventional test matrices, overall testing time and permits more focus on test analysis and modeling.

The foregoing description is provided to illustrate the invention, and is not to be construed as a limitation. Numerous additions, substitutions and other changes can be made to the invention without departing from its scope as set forth in the appended claims.

We claim:

1. A man-made specimen for measuring behavior of a material under multiple strain rates with only a single strain test comprising:
   a man-made body having a first end, a second end and a gage region disposed between the first end and the second end, wherein the body has a central, longitudinal axis passing through the first end and the second end, wherein the man-made body consists essentially of the same material throughout; and
   wherein the gage region comprises:
      a first gage section, having a first length along the central, longitudinal axis, and a second gage section, having a second length along the central, longitudinal axis, wherein the first gage section defines a first constant cross-sectional area along the first length that is defined by a first plane that extends through the first gage section and is perpendicular to the central, longitudinal axis and the second gage section defines a second constant cross-sectional area along the second length that is defined by a second plane that extends through the second gage section and is perpendicular to the central, longitudinal axis, wherein the first gage section and the second gage section are connected to one another by a step portion that has a non-linear profile as viewed along a direction perpendicular to the central, longitudinal axis; and
      a third gage section, having a third length along the central, longitudinal axis, wherein the third gage section defines a third constant cross-sectional area along the third length that is defined by a third plane that extends through the third gage section and is perpendicular to the central, longitudinal axis, wherein the first cross-sectional area, the second cross-sectional area and the third cross-sectional area are each unequal in size with one another.

2. The man-made specimen of claim 1, wherein the first gage section has a length as measured along the central, longitudinal axis that is the same as a length of the second gage section as measured along the central, longitudinal axis.

3. The man-made specimen of claim 1 wherein the first cross-sectional area and the second cross-sectional area are each for cylindrical cross section specimens.

4. The man-made specimen of claim 1, wherein the first cross-sectional area is larger in size than the second cross-sectional area, and the second cross-sectional area is larger in size than the third cross-sectional area.

5. The man-made specimen of claim 1, wherein the second gage section and the third gage section are connected to one another by a second step portion that has a second non-linear profile as viewed along a direction perpendicular to the central, longitudinal axis.

6. The man-made specimen of claim 5, wherein the first cross-sectional area is larger in size than the second cross-sectional area, and the second cross-sectional area is larger in size than the third cross-sectional area.

7. The man-made specimen of claim 1 wherein the first gage section and the second gage section are each cylinder shaped for cylindrical specimens.

8. A man-made specimen for measuring behavior of a material under multiple strain rates with only a single strain test comprising:
   a man-made body having a first end, a second end and a gage region disposed between the first end and the second end, wherein the body has a central, longitudinal axis passing through the first end and the second end;
      wherein the gage region comprises a first gage section and a second gage section along the central, longitudinal axis, that are not separated from one another, wherein the first gage section defines a first cross-sectional area that is defined by a first plane that extends through the first gage section and is perpendicular to the central, longitudinal axis and the second gage section defines a second cross-sectional area that is defined by a second plane that extends through the second gage section and is perpendicular to the central, longitudinal axis and wherein the first cross-sectional area is different in size than the second cross-sectional area; and
   wherein the gage region has a circular profile as viewed along a direction perpendicular to the central, longitudinal axis and wherein the circular profile for sheet metals has a radius R defined by an equation where $$R = \sqrt{L_0^2 + \frac{W_0^2}{4}\left(\frac{\sigma_{UTS}}{\sigma_{ys}} - 1\right)^2},$$

wherein $L_0$ is a distance from the midpoint of the specimen at which the specimen will yield when the midpoint fractures, $W_0$ is the width of the specimen at the midpoint, $\sigma_{UTS}$ is the ultimate tensile strength of the specimen and $\sigma_{ys}$ is the yield strength of the specimen.

9. A system for characterizing material behavior under multiple strain rates using a single specimen in one test comprising:
a device for applying a load, the device comprising a first jaw and a second jaw, the device capable of applying strain loads at greater than 500 inches per second;
a specimen having a body with a first end, a second end and a gage region disposed between the first end and the second end, wherein the first end is engaged by the first jaw and the second end is engaged by the second jaw, wherein the body has a central, longitudinal axis passing through the first end and the second end, wherein the gage region comprises a first gage section and a second gage section, wherein the first gage section defines a first cross-sectional area that is defined by a first plane that extends through the first gage section and is perpendicular to the central, longitudinal axis and the second gage section defines a second cross-sectional area that is defined by a second plane that extends through the second gage section and is perpendicular to the central, longitudinal axis and wherein the first cross-sectional area is different in size than the second cross-sectional area; and
a camera focused at the specimen and generates an image of the specimen; and
a control and data acquisition unit that receives signals from the camera representative of the image and calculates a strain experienced by the specimen based on the signals.

10. The system of claim 9, further comprising a second camera focused at the specimen and generates a second image of the specimen, wherein the control and data acquisition unit receives second signals from the second camera representative of the second image and calculates a strain experienced by the specimen based on the signals and the second signals.

11. The system of claim 10, wherein the control and data acquisition unit combines the first signals from camera one and the second signals from camera two to generate a three-dimensional image of the specimen.

12. The system of claim 11, wherein the control and data acquisition unit determines the strain based on the three dimensional image and a subsequent three-dimensional image of the specimen.

13. The system of claim 11, wherein the specimen comprises speckles, wherein the speckles are present in the three-dimensional image of the specimen.

14. The system of claim 13, wherein the control and data acquisition unit is able to track the position of each of the speckles and the control and data acquisition unit determines the strain based on first positions of the speckles in the three dimensional image and second positions of the speckles in a subsequent three-dimensional image of the specimen.

15. The system of claim 9, further comprising a sensor measuring a load applied to particular location of the specimen, wherein the sensor sends a signal representative of the load applied to the particular location to the control and data acquisition unit and the control and data acquisition unit determines a stress applied to the particular location based on the signal representative of the load and the signals from the camera representative of the image.

16. The system of claim 15, wherein the control and data acquisition unit controls collection of the signal representative of the load and synchronization of the signal with the signals from the camera representative of the image.

17. The system of claim 16 wherein the first cross-sectional area and the second cross-sectional are each for cylindrical cross section specimens and rectangular for sheet specimens.

18. The system of claim 17 wherein the first gage section and the second gage section are not separated from one another.

19. The system of claim 18 wherein the gage region has a circular profile as viewed along a direction perpendicular to the central, longitudinal axis.

20. The system of claim 19 wherein the circular profile has a radius R defined by an equation where $$R = \sqrt{L_0^2 + \frac{W_0^2}{4}\left(\frac{\sigma_{UTS}}{\sigma_{ys}} - 1\right)^2}$$

for sheet specimens, wherein $L_0$ is a distance from the midpoint of the specimen at which the specimen will yield when the midpoint fractures, $W_0$ is the width of the specimen at the midpoint, $\sigma_{UTS}$ is the ultimate tensile strength of the specimen and $\sigma_{ys}$ is the yield strength of the specimen.

21. The system of claim 9, wherein the control and data acquisition unit controls the testing of the specimen by the device.

22. The system of claim 9 wherein the first gage section and the second gage section are each for cylindrical cross section specimens.

23. The system of claim 22 wherein the first gage section and the second gage section are separated by a step portion.

24. The system of claim 23, wherein the first gage section has a length as measured along the central, longitudinal axis that is the same as a length of the second gage section as measured along the central, longitudinal axis.

25. A method for characterizing material behavior under multiple strain rates using a single specimen in one test comprising:
applying a load to a specimen having a body, wherein the body comprises:
a first end, a second end and a gage region disposed between the first end and the second end, wherein the load is applied to the first end, wherein the body has a central, longitudinal axis passing through the first end and the second end, wherein the gage region comprises:
a first gage section, having a first length along the central, longitudinal axis, and a second gage section, having a second length along the central, longitudinal axis, wherein the first gage section defines a first constant cross-sectional area along the first length that is defined by a first plane that extends through the first gage section and is perpendicular to the central, longitudinal axis and the second gage section defines a second constant cross-sectional area along the second length that is defined by a second plane that extends through the second gage section and is perpendicular to the central, longitudinal axis, wherein the first gage section and the second gage section are connected to one another by a step portion that has a non-linear profile as viewed along a direction perpendicular to the central, longitudinal axis; and
a third gage section, having a third length along the central, longitudinal axis, wherein the third gage section defines a third constant cross-sectional area along the third length that is defined by a third plane that extends through the third gage section and is perpendicular to the central, longitudinal axis, wherein the first cross-sectional area, the second cross-sectional area and the third cross-sectional area are each unequal in size with one another; and generating an image of the specimen when a first deformation is experienced by the specimen;

generating a second image of the specimen when a second deformation is experienced by the specimen;

calculating a strain experienced by the specimen at each of the first and second deformations.

26. The method of claim 25, wherein the method is performed at strain rates between 1 to 1000/s, wherein s denotes seconds.

27. The method of claim 25, wherein the first cross-sectional area is larger in size than the second cross-sectional area, and the second cross-sectional area is larger in size than the third cross-sectional area.

28. The method of claim 25, wherein the second gage section and the third gage section are connected to one another by a second step portion that has a second non-linear profile as viewed along a direction perpendicular to the central, longitudinal axis.

29. The method of claim 28, wherein the first cross-sectional area is larger in size than the second cross-sectional area, and the second cross-sectional area is larger in size than the third cross-sectional area.

30. The method of claim 25, wherein the body consists essentially of the same material throughout.

31. The method of claim 30, wherein the first cross-sectional area is larger in size than the second cross-sectional area, and the second cross-sectional area is larger in size than the third cross-sectional area.

32. The method of claim 30, wherein the second gage section and the third gage section are connected to one another by a second step portion that has a second non-linear profile as viewed along a direction perpendicular to the central, longitudinal axis.

33. The method of claim 32, wherein the first cross-sectional area is larger in size than the second cross-sectional area, and the second cross-sectional area is larger in size than the third cross-sectional area.

* * * * *